United States Patent [19]

Scheler et al.

[11] Patent Number: 5,077,395
[45] Date of Patent: Dec. 31, 1991

[54] SUBSTITUTED 1,2-NAPHTHOQUINONE-2-DIAZIDE-4-SULFONIC ACIDS AND PROCESSES FOR THEIR PREPARATION AND USE

[75] Inventors: Siegfried Scheler, Wiesbaden; Gerhard Buhr, Koenigstein; Klaus Bergmann, Mainz-Bretzenheim, all of Fed. Rep. of Germany

[73] Assignee: Hoechst Aktiengesellschaft, Frankfurt am Main, Fed. Rep. of Germany

[21] Appl. No.: 564,612

[22] Filed: Aug. 9, 1990

[30] Foreign Application Priority Data

Aug. 12, 1989 [DE] Fed. Rep. of Germany ....... 3926776

[51] Int. Cl.$^5$ ................ C07C 309/35; C07C 245/12; G03F 7/022
[52] U.S. Cl. .................... 534/557; 534/564; 430/193
[58] Field of Search .......... 534/556, 557, 564

[56] References Cited

U.S. PATENT DOCUMENTS

| 793,743 | 7/1905 | Sandmeyer | 534/557 |
|---|---|---|---|
| 2,987,513 | 6/1952 | Schmidt et al. | 534/569 |
| 3,931,255 | 1/1976 | Durholz et al. | 552/297 |
| 4,104,070 | 8/1978 | Moritz et al. | 430/191 |
| 4,576,901 | 3/1986 | Stahlhofen et al. | 430/325 |
| 4,777,246 | 10/1988 | Fötsch | 534/557 |

FOREIGN PATENT DOCUMENTS

| 212482 | 3/1987 | European Pat. Off. | |
| 283898 | 9/1988 | European Pat. Off. | |
| 0368085 | 5/1990 | European Pat. Off. | |
| 1126541 | 10/1962 | Fed. Rep. of Germany | |
| 3837500 | 5/1990 | Fed. Rep. of Germany | |
| 263982 | 1/1989 | German Democratic Rep. | |
| 237594 | 4/1926 | United Kingdom | 534/557 |

OTHER PUBLICATIONS

M. Gates, et al., "The Synthesis and Resolution of 3-Hydroxy-N-Methylisomorphinan", Journal of the American Chemical Society, vol. 80, Mar. 1958, pp. 1186–1191.

J. Kosar, "o-Quinone Diazides", Light-Sensitive Systems, pp. 339–344.

E. Mueller, "Methoden der Organischen Chemie", 1965, pp. 84–85.

Brandtstaedter et al., Chemical Abstracts, vol. 111, No. 96875y (1989).

V. Regitz, et al., "α-Diazocarbonylverbindungen", Diazoalkane Elgenschaften und Synthesen, 1977, pp. 129–134.

V. Sues, et al., "Photosynthese Des Fluorens, Des Reten-Fluorens und Des 1.2-Benzo-Fluorens", Annalen Der Chemie, 1958, pp. 20–25.

L. Homer, et al., Chemische Berichte, 1962, pp. 1206–1218.

E. L. Martin, et al., ¢1,2-Naphthoquinone-4-Sulfonate, Ammonium and Potassium ∞, Organic Syntheses, vol. 3, pp. 633–636.

Boniger, Berichte, 1894: 3050–3054.
Kaufler et al., Berichte, 1907:3269, 3274–76.
Clausius, Berichte, 1890:517–523.
Leonhardt et al., Theefarbenfabrikation, 1891:15.
Zusammenstellung der Patente Gebiete der Organischen Chemie, 1908:19.

Primary Examiner—Mary C. Lee
Assistant Examiner—Fiona T. Powers
Attorney, Agent, or Firm—Foley & Lardner

[57] ABSTRACT

Substituted 1,2-naphthoquinone-2-diazide-4-sulfonic acids are disclosed having the general formula A

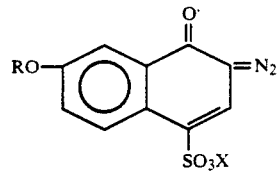

in which
R is an alkyl, epoxyalklyl, alkylcarbonyl or alkylsulfonyl group, the carbon chains of which may be interrupted by oxygen atoms, or a substituted or unsubstituted aralkyl, arylcarbonyl or arylsulfonyl group and
X is hydrogen, a metal or an ammonium group.

A process for the preparation of the compounds is also disclosed. The compounds can be used as such, or preferably after condensation of their sulfonic acid chlorides with aromatic hydroxy compounds or amines to give the corresponding esters or amides, as light-sensitive compounds in radiation-sensitive mixtures or materials.

15 Claims, No Drawings

SUBSTITUTED 1,2-NAPHTHOQUINONE-2-DIAZIDE-4-SULFONIC ACIDS AND PROCESSES FOR THEIR PREPARATION AND USE

BACKGROUND OF THE INVENTION

The present invention relates to substituted 1,2-naphthoquinone-2-diazide-4-sulfonic acids, and to processes for their preparation and use.

Esters, amides and hydrazides of 1,2-naphthoquinone-2-diazide-sulfonic acids have been used for many years as light-sensitive compounds for radiation-sensitive mixtures such as, for instance, photoresists for the production of semiconductor components in microelectronics or as coating solutions for the production of photomechanically processable printing forms or color proofing films. Suitable compounds and processing methods are described in J. Kosar, Light-Sensitive Systems, John Wiley & Sons, New York, chapter 7.4, 1965, U.S. Pat. No. 4,104,070, U.S. Pat. No. 4,576,901 and EP 0,212,482.

The preparation of the 1,2-naphthoquinone-2-diazide-sulfonic acids on which these known derivatives are based starts from a 1-naphthol-4- or -5-sulfonic acid which is nitrosated with an alkali metal nitrite in a dilute mineral acid. The resulting 2-nitroso-1-naphtholsulfonic acids are isolated, and the unconverted starting materials as well as the by-products formed in the nitrosation are removed by washing out or redissolution. The nitroso compound is then reduced in aqueous solution to the corresponding amino compound. The latter is isolated and again freed of unconverted starting materials and resulting by-products by digestion in water or by redissolution. The amino compound is then suspended in water and diazotized at a pH of 4–6 with an alkali metal nitrite in the presence of Cu(II) salts. In most cases, the 1,2-naphthoquinone-2-diazide-sulfonic acids obtained in this way must still be freed of dark-colored by—products formed in the diazotization by redissolution or recrystallization.

The disadvantage of this known preparation process is that the feed materials unconverted in the individual reaction stages and the by-products formed must be separated by additional purification steps from the desired main product. This entails low yields, a not always satisfactory product quality and high production costs.

EP 283,898 discloses a process for the preparation of benzoquinone- and naphthoquinonediazide-sulfonic acids, which may be substituted by halogen or by nitro or alkyl groups, and of salts thereof. In this case, the starting material is an arylsulfonic acid having at least one hydroxyl group. This acid is nitrosated in the known manner, the resulting nitroso compound is reduced in the alkaline pH range, and the amino compound is then converted into a sulfamate derivative which is subsequently mixed with a diazotizing agent. Acidification of the mixture produces the benzoquinone- or naphthoquinone-diazide-sulfonic acids. The reaction products formed after each reaction step are not isolated, but remain in solution for further reaction ("one-pot reaction"). By-products and impurities which arise in the individual process steps can be separated off in a satisfactory manner by filtering the reaction solution.

The disadvantage of this single-stage process is that the various process steps can be carried out only within a relatively narrow pH range and the reaction times, and reaction temperatures must be adhered to very exactly. The end products obtained by this process are generally not free of isomeric compounds. A universal industrial use of the compounds prepared by this process is therefore restricted.

In German Pat. application No. P 3,837,499.4, which is not a prior publication, a process for the preparation of esters of ring-substituted 1,2-naphthoquinone-2-diazide-4-sulfonic acids is described, wherein 1,2-naphthoquinone-2-diazide-4-sulfonic acids, which are substituted in the 5-, 6-, 7- or 8-position by halogen, alkoxy or alkoxycarbonyl, are obtained as intermediates.

In this case, the starting material is an appropriately substituted 2-naphthol which is nitrosated in the 1-position. The product is sulfonated in the 4-position with an alkali metal hydrogen sulfite and the nitroso group is then reduced to the amino group by acidification with a mineral acid at a pH of about 7 or less. The 2-amino-1-naphthol-4-sulfonic acid is oxidized to the corresponding 1,2-naphthoquinone-4-sulfonic acid and the latter is converted with p-toluenesulfonic acid hydrazide in an organic solvent at temperatures of 20–10? C. to the corresponding ring-substituted,1,2-naphthoquinone-2-diazide-4-sulfonic acid.

Chlorination with chlorosulfonic acid or a chlorosulfonic acid/thionyl chloride mixture gives in a known manner the sulfonic acid chloride which is then condensed with a phenolic component to give the corresponding ring-substituted 1,2-naphthoquinone-2-diazide-4-sulfonic acid esters. The individual process steps for preparing the intermediates and end products are known from the literature. The process is dependent on the relatively poor accessibility of the substituted 2-naphthols which are used as the starting materials. Thus, for example, 7-alkoxy-2-naphthol is obtained according to a known process by monoalkylation of 2,7-dihydroxynaphthalene in a yield of only about 50–55% of theory. The yields of the subsequent reaction stages—nitrosation, sulfonation and reduction, oxidation, introduction of the diazo group—are satisfactory. In spite of the omission of additional purification of the intermediates, the overall yield of 7-alkoxy-1,2-naphthoquinone-2-diazide-4-sulfonic acid, relative to the 2,7-dihydroxynaphthalene employed, is not yet satisfactory, so that the production costs for the sulfonic acid esters which can be prepared are relatively high.

A further process for the preparation of ring-substituted 1,2-naphthoquinone-2-diazide-4-sulfonic acids, which can be used for synthesizing the corresponding esters and amides, is indicated in German Pat. application No. P 3,837,500.1, which is not a prior publication. For the preparation of 7-methoxy-1,2-naphthoquinone-2-diazide-4-sulfonic acid, the starting material is, for example, commercially-available 1-acetylamino-7-naphthol. This can be converted to the desired compound in a 7-stage reaction sequence methylation of the phenolic hydroxyl group, elimination of the acetyl group and preparation of 1-amino-7-methoxynaphthalene hydrogen sulfate, sulfonation in the 4-position by dry heating ("baking reaction"), replacement of the amino group by a hydroxyl group ("Bucherer reaction"), nitrosation in the 2-position, reduction of the nitroso group to the amino group and diazotization. Because of the multi-stage process, process steps which are difficult to carry out on an industrial scale, and the not always satisfactory yield of individual intermediates, this preparation process also raises industrial problems. It is, however, of the greatest importance for the production of photoresists to have available an economical synthesis process for the radiation-sensitive components.

DD 263,982 has disclosed the preparation of 2-diazo-1-oxo-1,2-dihydronaphthalene derivatives, starting from 1,7-dihydroxynaphthalene derivatives. The 1,7-dihydroxynaphthalene-4-sulfonic acid serving as the starting material for this purpose is, however, not easily accessible, so that it is very expensive to carry out the overall process. Moreover, the diazotization of the amino intermediate is possible in acceptable quality only under defined pH and temperature conditions and in the presence of heavy metal salts, and only in a low yield.

The esters and amides of 7-methoxy-1,2-naphthoquinone-2-diazide-4-sulfonic acid are, because of the shift of their absorption to longer wavelengths and because of their high reversal potential, outstandingly suitable for use in photoresist layers which can be structured in the g line (436 nm) and i line (365 nm) regions and can be processed either positively or negatively.

SUMMARY OF THE INVENTION

It was therefore an object of the invention to provide a process for the preparation of 1,2-naphthoquinone-2-diazide-4-sulfonic acids substituted in the 7-position, and derivatives thereof, which avoids the disadvantages of the known processes.

It is a further object of the present invention to provide a process for the production of acids, salts, esters and amides for photoresists, which process has a good yield, does not require additional purification of the intermediates, and has process steps which are simple in terms of production engineering.

In accordance with these and other objects of the invention, a process is provided for preparing a substituted 1,2-naphthoquinone-2-diazide-4-sulfonic acid or a salt thereof of the formula A

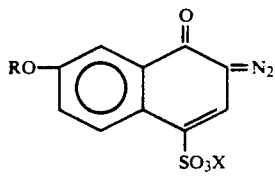

in which
  R is an alkyl, epoxyalkyl, alkylcarbonyl or alkylsulfonyl group, the carbon chains of which may be interrupted by oxygen atoms, or a substituted or unsubstituted aralkyl, arylcarbonyl or arylsulfonyl group and
  X is hydrogen, a metal or an ammonium group, comprising the steps of nitrosating 2,7-dihydroxynaphthalene; sulfonating the resulting 2,7-dihydroxy-1-nitrosonaphthalene (I) with an alkali metal hydrogen sulfite; reducing the bisulfite addition compound formed in acidic solution without intermediate isolation to 2,7-dihydroxy-1-aminonaphthalene-4-sulfonic acid (II); oxidizing the 2,7-dihydroxy-1-aminonaphthalene-4-sulfonic acid to 7-hydroxy-1,2-naphthoquinone-4-sulfonic acid (III) and precipitating the acid as a salt; converting the salt with an arylsulfonic acid hydrazide to the corresponding salt of 7-hydroxy-1,2-naphthoquinone-2-diazide-4-sulfonic acid (IV); converting this salt in aqueous alkali at temperatures between about 20 and 30° C. and at a pH of 11–12 with an alkylating or acylating agent to the corresponding salt of the compound of formula A substituted in the 7-position; and isolating the salt, and optionally converting this salt to the corresponding acid.

In particular, a substituted 1,2-naphthoquinone-2-diazide-4-sulfonic acid of the formula A

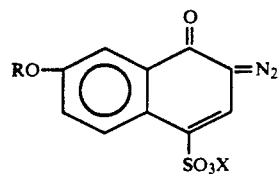

can be produced in which
  R is an epoxyalkyl, alkylcarbonyl or alkylsulfonyl group, the carbon chains of which may be interrupted by oxygen atoms, or a substituted or unsubstituted aralkyl, arylcarbonyl or arylsulfonyl group and
  X is hydrogen, a metal or an ammonium group.

The present invention also provides a radiation-sensitive mixture comprising a radiation-sensitive compound or an ester or amide of a compound as described above.

The present invention further provides a radiation-sensitive material comprising a support and a radiation-sensitive layer comprising a compound or an ester or amide of a compound as described above.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The compounds according to the invention are of the general formula A

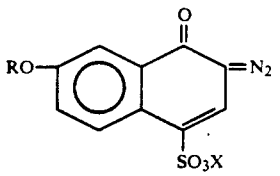

in which
  R is an epoxyalkyl, alkylcarbonyl or alkylsulfonyl group, the carbon chains of which may be interrupted by oxygen atoms, or a substituted or unsubstituted aralkyl, arylcarbonyl or arylsulfonyl group, and
  X is hydrogen, a metal or an ammonium group.
Preferably,
  R is an epoxyalkyl group having 3 to 6 carbon atoms, an alkylcarbonyl group having 2 to 6 carbon atoms or an alkylsulfonyl group having 1 to 4 carbon atoms, the carbon chains of which groups may be interrupted by at least one oxygen atom, or an aralkyl group having 7 to 10 carbon atoms, an arylcarbonyl group having 7 to 10 carbon atoms, or an arylsulfonyl group having 6 to 10 carbon atoms, which groups may be substituted by alkyl, trihalogenoalkyl, alkoxy, alkylcarbonyl or alkylsulfonyl groups or halogen, and X is an alkali metal or alkaline earth metal, for example, potassium or sodium, or the ammonium group.

In accordance with the present invention, a process is provided for the preparation of these substituted 1,2-naphthoquinone-2-diazide-4-sulfonic acids, and salts thereof, wherein 1) 2,7-dihydroxynaphthalene is nitrosated,
2) the resulting 2,7-dihydroxy-1-nitrosonaphthalene (I) is sulfonated with an alkali metal hydrogen sulfite and the bisulfite addition compound formed is reduced in acidic solution without intermediate isolation to 2,7-dihydroxy-1-aminonaphthalene-4-sulfonic acid (II),
3) the latter is oxidized to 7-hydroxy-1,2-naphthoquinone-4-sulfonic acid (III) and precipitated as a salt,
4) the salt is converted with an arylsulfonic acid hydrazide to the corresponding salt of 7-hydroxy-1,2-naphthoquinone-2-diazide-4-sulfonic acid (IV) and
5) the salt, preferably the alkali metal salt, is converted in aqueous alkali at temperatures between 20 and 30° C. and at a pH of 11–12 with an alkylating or acylating agent to the corresponding salt of the compound, substituted in the 7-position, of the general formula A, and this salt is isolated.

Preferably, the process relates to the preparation of compounds of the formula A in which R is an alkyl group having 1 to 6 carbon atoms, preferably having 1 to 4 and especially 1 or 2 carbon atoms, an epoxyalkyl group having 3 to 6 carbon atoms, an alkylcarbonyl group having 2 to 6 carbon atoms or an alkylsulfonyl group having 1 to 4 carbon atoms, the carbon chains of which groups may be interrupted by at least one oxygen atom, or an aralkyl group having 7 to 10 carbon atoms, an arylcarbonyl group having 7 to 10 carbon atoms or an arylsulfonyl group having 6 to 10 carbon atoms, which groups may be substituted by alkyl, trihalogenoalkyl, alkoxy, alkylcarbonyl or alkylsulfonyl groups or by halogen, and X is an alkali metal or alkaline earth metal, for example, potassium or sodium, or the ammonium group.

The process according to the invention proceeds in accordance with the following reaction diagram.

Reaction diagram

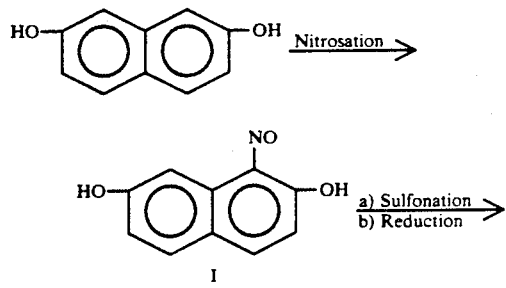

-continued
Reaction diagram

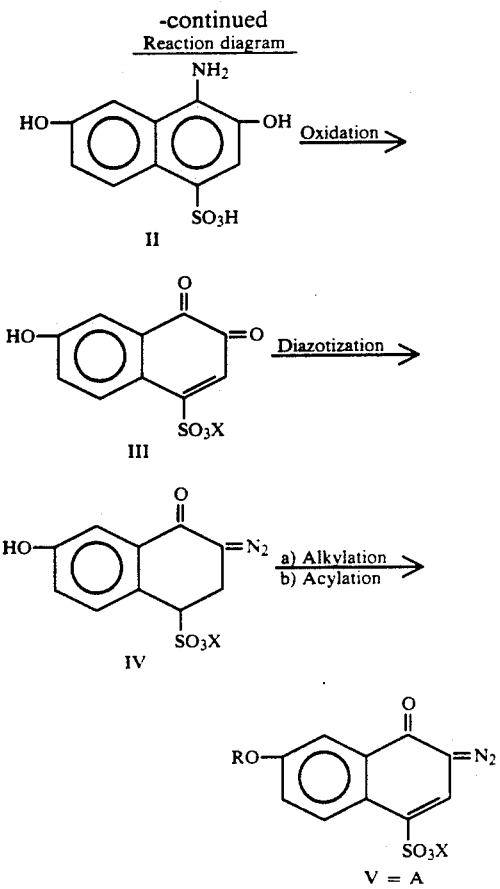

V = A

A particular advantage of the process according to the invention is that no additional purification steps of the individual intermediates are necessary so that a good yield of end product according to the general formula A is ensured.

The compounds of the general formula A can be used as light-sensitive compounds in radiation-sensitive mixtures. Alternatively, they can be converted via the intermediate stage of their sulfonic acid chlorides in a known manner by condensation with aromatic monohydroxy or polyhydroxy compounds or with aromatic, preferably polynuclear primary or secondary amines to the corresponding esters or amides, respectively, and used in light-sensitive mixtures and materials.

The preparation process according to the invention starts from commercially-available 2,7-dihydroxynaphthalene which can be converted in a known manner by nitrosation with sodium nitrite at temperatures between about 0 and 5° C. either in an aqueous suspension containing a mineral acid (Clausius, Chem. Ber. 23, 517 (1890); Leonhardt & Co., German Pat. No. 55,204 (1889)) or in a solution-containing acetic acid (Kaufler and Brauer, Chem. Ber,. 40, 3275 (1907)) to 2,7-dihydroxy-1-nitrosonaphthalene (I) or to the tautomeric 7-hydroxy-1,2-naphthoquinone-(1)-oxime (Ia). The yield and quality of the 2,7-dihydroxy-1-nitrosonaphthalene (I) are not satisfactory by either of the known processes.

Very surprisingly, however, the nitrosation of 2,7-dihydroxynaphthalene analogously to the method described by Gates and Webb in J. Am. Chem. Soc. 80,1186 (1958), for the preparation of 6-methoxy-1-nitroso-2-naphthol, proceeds in an almost quantitative reaction and very good purity. According to this method, sodium nitrite is added with vigorous stirring at +5 to −10° C. to a finely disperse suspension of 2,7-dihydroxynaphthalene, which is obtained by precipitating 2,7-dihydroxynaphthalene with ice from a warm solution containing acetic acid. The resulting dark-red microcrystalline nitroso/oxime compound (I/Ia) is filtered off with suction, washed with water until neutral and, if desired, dried. The reaction product obtained by this procedure is processed further without purification, preferably as a product moist with water.

According to the invention, the nitrosation is carried out in an aqueous suspension containing acetic acid with an alkali metal nitrite at temperatures between about +5 and −10° C. and the nitroso compound is isolated.

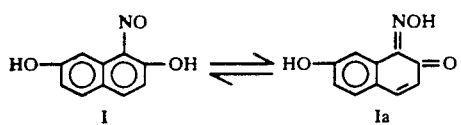

In the second reaction stage, the 2,7-dihydroxy-1-nitrosonaphthalene (I), which as a rule is still moist with water and reacts in the tautomeric oxime form (Ia), is first suspended, according to Boninger, Chem. Ber. 27, 3050 (1894), in commercially-available 37% aqueous sodium hydrogen sulfite solution and stirred at about 20°–25° C. until it is completely dissolved. The bisulfite addition compound (IIa) thus formed is not isolated, but the brown reaction solution is acidified with hydrochloric acid and heated to about 25°–60° C., 2,7-dihydroxy-1-aminonaphthalene-4-sulfonic acid (II) being formed by reduction of the nitroso group and aromatization of the cycloaliphatic ring system. The aminonaphtholsulfonic acid (II) is isolated by filtering off with suction the light-gray crystals formed, washing the crystals on the suction filter, first with water and then with methanol and, if desired, drying them. The reaction product thus prepared is used without further purification, if appropriate while still moist, for the next reaction stage. The yield of reaction product II is about 90–95% of theory.

The sulfonation is generally carried out with an alkali metal hydrogen sulfite in aqueous phase in a pH range of about 5–7 and the bisulfite addition compound formed is reduced, without intermediate isolation, in an aqueous solution containing a mineral acid at temperatures between about 20 and 60° C. to the corresponding aminosulfonic acid.

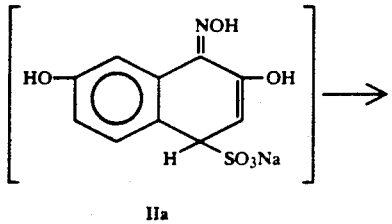

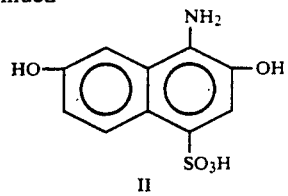

When carrying out the reaction in practice, it is more advantageous to use solid, more stable sodium disulfite in place of the commercially-available sodium hydrogen sulfite solution.

In the third reaction stage, 2,7-dihydroxy-1-aminonaphthalene-4-sulfonic acid (II) is oxidized with an oxidizing agent to 7-hydroxy-1,2-naphthoquinone-4-sulfonic acid (III).

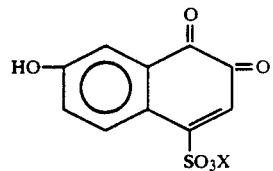

Examples of suitable oxidizing agents are potassium peroxydisulfate (K$_2$S$_2$O$_8$), Cr(VI) oxide, Pb(IV) oxide, Fe(III) chloride, chlorine, bromine or nitrous acid. Preferably, however, dilute nitric acid is used as the oxidizing agent. The 7-hydroxy-1,2-naphthoquinone-4-sulfonic acid (III) is usually isolated as the ammonium salt or as an alkali metal salt.

When nitric acid is used, the procedure is advantageously analogous to that described by Martin and Fieser in Org. Synth. Coll., Vol. III, 633 (1955). The oxidation preferably takes place at temperatures between about 15 and 25° C., the solid aminonaphtholsulfonic acid generally being introduced in portions with stirring into the nitric acid. Advantageously, dilute nitric acid is used, in order to maintain the reaction mixture, which is in the form of a suspension, in a state in which it can be stirred, and in order to be able more readily to limit the exothermically proceeding oxidation to room temperature by means of external cooling. About 15 to 25%, and preferably about 18–22%, aqueous nitric acid has proven particularly suitable as the oxidizing agent.

The 7-hydroxy-1,2-naphtho-quinone-4-sulfonic acid (III) formed is preferably precipitated as the ammonium salt or potassium salt by salting out with ammonium chloride or potassium chloride, respectively, and is isolated by filtration. The filter residue is washed with a saturated solution of ammonium chloride or potassium chloride, respectively, and then with ethanol and, if desired, dried at about 20°–40 C. The salts of 7-hydroxy-1,2-naphthoquinone-4-sulfonic acid prepared in this way contain as a rule small proportions (about 2–3%) of 7-hydroxy-1,2-naphthoquinone-1-diazide-4-sulfonic acid (IVa). This is formed in a side reaction by diazotization of the 2,7-dihydroxy-1-amino-naphthalene-4-sulfonic acid employed with nitrous acid which is present in the oxidation medium when nitric acid is used. However, this by-product forms in only a small quantity and does not interfere with the subsequent conversion to 7-hydroxy-1,2-naphthoquinone-2-diazide-4-sulfonic acid (IV), because the salts of the isomeric 7-hydroxy-1,2-naphthoquinone-1-diazide-4-sulfonic acid (IVa) are more readily soluble than the desired salts of 7-hydroxy-1,2-naphthoquinone-2-diazide-4-sulfonic acid (IV). When more highly concentrated nitric acid is used, the proportion of 7-hydroxy-1,2-naphthoquinone-1-diazide-4-sulfonic acid (IVa) increases.

Accordingly, the oxidation is preferably carried out with about 15 to 25% by weight aqueous nitric acid at temperatures between about 15 and 25° C., the naphthoquinonesulfonic acid formed is precipitated as the ammonium salt or potassium salt, and the salt is isolated.

Significantly greater quantities (about 20–40%) of 7-hydroxy-1,2-naphthoquinone-1-diazide-4-sulfonic acid (IVa) are formed by the oxidation method, described by Boninger in Chem. Ber.27, 3050 (1894), in dilute hydrochloric acid with sodium nitrite at about 0 to 5° C. According to this known procedure, the potassium salts of the desired 7-hydroxy-1,2-naphthoquinone-4-sulfonic acid (III) and of the undesired 7-hydroxy-1,2-naphthoquinone-1-diazide-4-sulfonic acid (IVa) are precipitated together from the red-brown solution by salting out with potassium chloride. A separation of the potassium salts of these two sulfonic acids by fractional crystallization is possible in principle, but involves large losses. This oxidation method is therefore unsuitable for an industrial production process.

In the fourth reaction stage, the ammonium salt or the alkali metal salts, preferably the potassium salt, of 7-hydroxy-1,2-naphthoquinone-4-sulfonic acid (III) are converted with an arylsulfonic acid hydrazide, for example, p-toluenesulfonic acid hydrazide, in an aqueous suspension, but preferably in an alcoholic suspension, for example, in methanol, at temperatures between about 20 and 70° C., preferably about 20 and 30° C., with high regioselectivity to the corresponding salts of 7-hydroxy-1,2-naphthoquinone-2-diazide-4-sulfonic acid (IV). The isomeric salts, still to be expected, of 7-hydroxy-1,2-naphthoquinone-1-diazide-4-sulfonic acid (IVa) are formed under these reaction conditions in only extremely small proportions (about 1–2%).

Preferably, the ammonium salt or potassium salt of the naphthoquinonesulfonic acid is converted with p-toluenesulfonic acid hydrazide in aqueous or organic phase at temperatures between about 20 and 70° C. to the corresponding salts of 7-hydroxy-1,2-naphthoquinone-2-diazide-4-sulfonic acid and this salt is isolated.

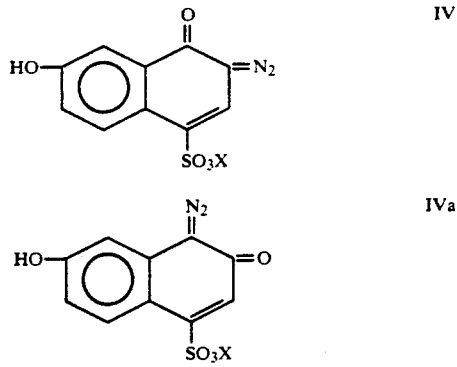

The excellent regioselectivity in this reaction is surprising, inasmuch as the isomer ratio of the substituted o-benzoquinone-diazides, prepared by Horner and Durckheimer and described in Chem. Ber. 95,1206 (1962), in some cases differs very significantly from the isomer mixture of the above-mentioned substituted naphthoquinonediazides.

7-Hydroxy-1,2-naphthoquinone-2-diazide-4-sulfonic acid (IV) and its salts have hitherto not been described in the literature. By reactions on the phenolic hydroxyl group, for example, alkylation or acylation, or on the sulfonic acid group, for example, chlorination, it is possible in a very simple manner to prepare the substituted 1,2-naphthoquinone-2-diazide-4-sulfonic acids of the general formula A, and the as yet unknown 7-hydroxy-1,2-naphthoquinone-2-diazide-4-sulfonic acid chloride.

The replacement of an oxygen atom in α-diketones by the diazo group with an arylsulfonic acid hydrazide is known from the literature as the "Bamford-Stevens reaction." In this reaction, a diketone arylhydrazone is formed as an intermediate, which can be cleaved to give an α-diazo-carbonyl compound under very simple and mild reaction conditions, with or without using alkali.

In DE 1,126,541, such a reaction is described for the preparation of 6-nitro-1,2-naphthoquinone-2-diazide-4,8-disulfonic acid from 6-nitro-1,2-naphthoquinone-4,8-disulfonic acid by reaction with an arylsulfonic acid hydrazide and subsequent cleavage of the primarily formed hydrazone in an aqueous alkaline medium. An isolation of the naphthoquinone-diazide derivative as such is not necessary for the preparation process, described here, for special azo dyes.

A further application of the Bamford-Stevens reaction has been described by Sus, Steppan and Dietrich in Liebigs Ann. Chem. 617;20 (1958), for the preparation of polycyclic aromatic o-quinonediazides, for example, phenanthrenequinone-9,10-diazide and chrysenequinone-5,6-diazide. These o-quinonediazides are obtained by reacting the corresponding polycyclic o-quinones with p-toluene-sulfonic acid hydrazide in ethanol at temperatures between about 45 and 60° C. and subsequent cleavage of the toluenesulfonic acid hydrazones formed as intermediates, without using alkali.

Summarizing reports on the range of application and on the different process variants of the Bamford-Stevens reaction are to be found in the specialist literature (M. Regitz, Diazoalkane [Diazoalkanes], chapter 5.3, 129 (1977), or HoubenWeyl, Aromatische Diazoniumsalze [Aromatic Diazonium Salts], volume 10/3, 84).

The procedure for the preparation of the ammonium salt or potassium salt of 7-hydroxy-1,2-naphthoquinone-2-diazide-4-sulfonic acid (IV) is advantageously such that the corresponding salts of 7-hydroxy-1,2-naphthoquinone-4-sulfonic acid (III) are suspended in water or in a polar organic solvent, preferably methanol, and the p-toluene-sulfonic acid hydrazide is added with stirring at temperatures between about 15 and 30° C. The reaction mixture is heated to between about 20 and 40° C. with continued stirring. When a polar organic solvent, for example, methanol, is used as the reaction medium, the initially dark-red suspension of the salts of 7-hydroxy-1,2-naphthoquinone-4-sulfonic acid changes, generally without noticeable dissolution, into a yellow suspension. The ammonium salts or potassium salts of 7-hydroxy-1,2-naphthoquinone-2-diazide-4-sulfonic acid obtained in high yields by this procedure are isolated from the reaction mixture by simple filtration and washed with plenty of methanol. Additional purification, for example, reprecipitation or recrystallization, is not necessary.

The use of a polar solvent such as, for example, methanol as the reaction medium is particularly advantageous because the resulting ammonium salt or potassium salt of 7-hydroxy-1,2-naphthoquinone-2-diazide-4-sulfonic acid is only very sparingly soluble in this solvent. The small proportions of impurities originating from the starting material and the p-toluenesulfinic acid formed in the hydrazone cleavage are, however, very readily soluble in methanol, so that the yield of pure reaction product is very high according to this procedure.

In the aqueous procedure, the yellow suspension formed after the reaction with p-toluenesulfonic acid hydrazide is dissolved by heating to temperatures between about 40 and 50° C., and the yellow-brown solution is freed from a small quantity of dark products by means of an adsorbent, for example activated carbon, and the reaction product is precipitated from the clear filtrate by salting out with ammonium chloride or potassium chloride and cooling to about 0–5° C. The yield and purity according to this procedure are lower than those according to the preferred method in methanol as the reaction medium.

The substituted 1,2-naphthoquinone-2-diazide-4-sulfonic acids according to the invention, of the general formula A

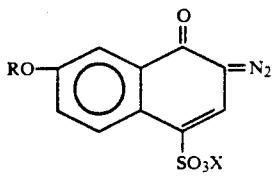

in which R and X have the meanings given above, surprisingly are obtained in a very high yield and in excellent purity from the salts, preferably the potassium salt, of 7-hydroxy-1,2-naphthoquinone-2-diazide-4-sulfonic acid (IV). The salt is reacted in aqueous alkaline solution at temperatures between about 20 and 50° C., preferably between about 20 and 25° C., at a pH of 11–12 with an alkylating agent, for example, an alkyl halide, aralkyl halide, epoxyalkyl halide or a sulfonic acid ester, or with an acylating agent, for example, an aromatic carboxylic or sulfonic acid halide. The reaction products, which are generally in a crystalline form, are isolated by filtration. An additional purification of the crude products for further processing is in most cases unnecessary.

Aliphatic sulfonic acid esters, for example, a dialkyl sulfate such as dimethyl sulfate or diethyl sulfate, are preferably used as the alkylating agent for the preparation of 7-alkoxy-1,2-naphthoquinone-2-diazide-4-sulfonic acids of the general formula A. In principle, however, aromatic sulfonic acid esters, for example, p-toluenesulfonic acid esters, are also suitable, particularly in the presence of "phase transfer catalysts," for example, tetrabutylammonium bromide or benzyltriethylammonium bromide.

For the preparation of the 7-epoxyalkoxy-1,2-naphthoquinone-2-diazide-4-sulfonic acids of the general formula A, the alkylating agents used are epoxyalkyl halides, preferably epoxypropyl bromide or epichlorohydrin, and for the preparation of the 7-arylalkyl-1,2-naphthoquinone-2-diazide-4-sulfonic acids of the general formula A, aralkyl halides, for example, benzyl bromide or benzyl chloride, are used.

The acylating agents used for the preferred 7-arylcarbonyloxy- and 7-arylsulfonyloxy-1,2-naphthoquinone-2-diazide-4-sulfonic acids of the general formula A are arylcarboxylic acid halides, for example, benzoyl chloride, 2-methylbenzoyl chloride or 4-methylbenzoyl chloride, or arylsulfonic acid halides, for example, benzene-sulfonic acid chloride or p-toluenesulfonic acid chloride.

The aliphatic 7-alkylcarbonyloxy-1,2-naphthoquinone-2-diazide-4-sulfonic acids of the general formula A are more readily obtained by reacting 7-hydroxy-1,2-naphthoquinone-2-diazide-4-sulfonic acid with alkylcarboxylic acid chlorides or alkylcarboxylic acid anhydrides in glacial acetic acid in the presence of anhydrous zinc chloride.

The surprisingly easy course of the alkylation and acylation reactions is due to the high stability of 7-hydroxy-1,2-naphthoquinon-1-4-sulfonic acid in aqueous alkaline solution. It is also surprising that 7-hydroxy-1,2-aphthoquinone-2-diazide-4-sulfonic acid as a substituted 2-naphthol derivative does not couple in alkaline solution to give an azo dye ("self-coupling").

The substituted 1,2-naphthoquinone-2-diazide-sulfonic acids of the general formula A, preferably 7-methoxy-1,2-naphthoquinone-2-diazide-4-sulfonic acid, are valuable intermediates for the production of radiation-sensitive esters or amides. These derivatives are obtained from 7-methoxy-1,2-naphthoquinone-2-diazide-4-sulfonic acid in a known manner by chlorination with chlorosulfonic acid or a chlorosulfonic acid/thionyl chloride mixture and subsequent condensation of the resulting sulfonic acid chloride with preferably aromatic monohydroxy or polyhydroxy compounds or polynuclear primary or secondary amines.

The radiation-sensitive esters and amides of 7-methoxy-1,2-naphthoquinone-2-diazide-4-sulfonic acid can advantageously be used industrially for radiation-sensitive mixtures, for example, as a photoresist for the production of semiconductor components in microelectronics or for the photomechanical production of printing forms or color proofing films.

The invention is explained in more detail by the examples which follow, without limiting it thereto.

2,7-Dihydroxy-1-nitrosonaphthalene (I)

2,7-Dihydroxynaphthalene (BAYER) (250 g=1.56 mol) were dissolved at 0°–90° C. in 875 ml of glacial acetic acid and precipitated by addition of 2.5 kg of crushed ice. A very finely disperse, light-beige, viscous suspension was formed, and the temperature fell to −10 to −12° C. With good stirring and external cooling, 107.88 g (1.56 mol) of solid sodium nitrite were introduced in portions into this suspension, the mixture was stirred for another hour and a further 10.7 g (0.56 mol) of solid sodium nitrite were then added. Stirring was then continued for a further 2 hours at −8 to −5° C., and the 2,7-dihydroxy-1-nitrosonaphthalene arose as dark-red crystals which were filtered off with suction and well pressed off on the suction filter. The reaction product, while still moist from the suction filter, was then stirred into 5 l of water at 20°–25° C. for about one hour, filtered off again with suction, well pressed off and dried for 24 hours in a circulating-air oven at 20°–25° C. Yield: 294 g of pure product (=99.6% of theory)

Characteristic data
Appearance: dark-red, finely disperse powder
Melting point:
  140°–145° C. (brightening)
  ≧195° C. (charring without melting)
Elemental analysis Empirical formula: $C_{10}H_7O_3N$
Molecular weight: 189

|  | C | H | N |
|---|---|---|---|
| Calculated: | 63.5 | 3.7 | 7.4 |
| Found: | 63.7 | 3.7 | 7.1 |

2,7-Dihydroxy-1-aminonaphthalene-4-sulfonic acid. 2 $H_2O$ (II)

2,7-Dihydroxy-1-nitrosonaphthalene (I) (200 g = 1.06 mol) were suspended in 1.75 l of water at 20°-25° C., and 67 g (0.8 mol) of sodium hydrogen carbonate were slowly added in portions with stirring, initial foaming being prevented by addition of 1 ml of n-octanol. Sodium disulfite ($Na_2S_2O_5$) (225 g = 1.2 mol) were then added and the mixture was stirred for 17 hours at 20°-25° C., the initially red suspension changing into a brown solution. A small quantity of dark resinous products was then separated off by filtering the solution over activated carbon, 660 ml of 37% hydrochloric acid were added to the now clear brown filtrate until the latter showed an acidic reaction to congo red, and the mixture was heated for 75 minutes at 40°-50° C. with stirring. During this time, part of the reaction product precipitated, with evolution of $SO_2$. After cooling of the reaction mixture to 20°-25° C. and standing for 24 hours, the precipitated light-gray crystals were filtered off with suction, and were well pressed off and washed on the suction filter first with 500 ml of water and then with 1 l of methanol, until the methanol phase running off showed only a slight yellow color. After drying in a circulating-air oven at 20°-25° C., the 2,7-dihydroxy-1-aminonaphthalene-4-sulfonic acid, which still contained 2 mol of water of crystallization, was obtained as a light-gray powder.

Yield: 288 g of pure product (= 90.5% of theory)
Characteristic data
Appearance: light-gray powder
Melting point: $\geq 275°$ C. (decomposition)
Elemental analysis
Empirical formula: $C_{10}H_9O_5NS.2\ H_2O$
Molecular weight: 291

|  | C | H | N | S | $H_2O$ |
|---|---|---|---|---|---|
| Calculated: | 41.2 | 4.5 | 4.8 | 11.0 | 12.4 |
| Found: | 41.8 | 4.2 | 4.6 | 10.9 | 12.1 |

7-Hydroxy-1,2-naphthoquinone-4-sulfonic acid (K salt). 1 $H_2O$ (III)

An amount of a 19% nitric acid solution (219 g = 0.662 mol) was cooled to 15° C. and 1.5 g (5.2×10⁻³ mol) of 2,7-dihydroxy-1-aminonaphthalene-4-sulfonic acid. 2 $H_2O$ (II) were introduced with stirring. After the oxidation reaction had been started with about 1 ml of 65% nitric acid, the remaining 148.5 g (0.51 mol) of 2,7-dihydroxy-1-aminonaphthalene-4-sulfonic acid. 2 $H_2O$ were slowly introduced in portions at 15°-20° C. in the course of 2 hours with continued stirring into the dark-red solution formed. It was possible greatly to reduce initial foaming by the addition of a few drops of n-octanol. After all the 2,7-dihydroxy-1-aminonaphthalene-4-sulfonic acid. 2 $H_2O$ had been added, the mixture was stirred for a further 30 minutes at 15°-20° C. and the dark-red suspension was then stirred into 1.6 l of water at 50° C. This gave a clear, dark-red solution. Potassium chloride (170 g) in portions of about 25 g each was introduced into this solution. The precipitation of shiny red crystals from the solution started when the first 25 g of potassium chloride were added. The reaction mixture was cooled to 0 to 5° C. and filtered with suction after two hours, and the suction filter content was washed first with 80 ml of saturated potassium chloride solution and then with 160 ml of ethanol, and well pressed off. The filter residue was then dried in the circulating-air oven at 20°-25° C.

The crude 7-hydroxy-1,2-naphthoquinone-4-sulfonic acid (K salt) thus prepared also contained, in addition to potassium chloride, small proportions of 7-hydroxy-1,2-naphthoquinone-1-diazide-4-sulfonic acid (K salt) and 1 mol of water of crystallization.

The pure 7-hydroxy-1,2-naphthoquinone-4-sulfonic acid (K salt) was obtained by reprecipitation of the crude product from water.

Yield: 148 g of crude product (89% quality),
131.7 g of pure product (100% quality),
i.e., 82.4% of theory.
Characteristic data
Appearance: dark-red, crystalline powder
Melting point: $\geq 275°$ C. (decomposition)
Elemental analysis
Empirical formula: $C_{10}H_5O_6SK.1\ H_2O$
Molecular weight: 310

|  | C | H | S | $H_2O$ |
|---|---|---|---|---|
| Calculated: | 38.7 | 2.3 | 10.3 | 5.8 (%) |
| Found: | 38.8 | 2.1 | 9.9 | 6.1 (%) |

7-Hydroxy-1,2-naphthoquinone-4-sulfonic acid ($NH_4$ salt).1 $H_2O$ (III a)

The ammonium salt of 7-hydroxy-1,2-naphthoquinone-4-sulfonic acid was obtained by cooling the suspension, formed after the oxidation with nitric acid, to 0°-5° C. and adding saturated ammonium chloride solution with stirring. After two hours, the red suspension was filtered with suction, and the filter residue was washed on the suction filter first with saturated ammonium chloride solution and then with ethanol, well pressed off and dried in a circulating-air oven at 20°-25° C.

The 7-hydroxy-1,2-naphthoquinone-4-sulfonic acid ($NH_4$ salt) thus obtained also contained, in addition to ammonium chloride, small proportions of 7-hydroxy-1,2-naphthoquinone-1-diazide-4-sulfonic acid ($NH_4$ salt) and 1 mol of water of crystallization.

The pure 7-hydroxy-1,2-naphthoquinone-4-sulfonic acid ($NH_4$ salt) was obtained by reprecipitation of the crude product from water.

Yield: 125 g of crude product (93.40% quality),
117.7 g of pure product (100% quality),
i.e., 78.5% of theory.
Characteristic data
Appearance: dark-red, crystalline product
Melting point: $\geq 215°$ C. (decomposition)
Elemental analysis
Empirical formula: $C_{10}H_9NO_6S.1\ H_2O$
Molecular weight: 289

|  | C | H | N | S | $H_2O$ |
|---|---|---|---|---|---|
| Calculated: | 41.5 | 3.8 | 4.8 | 11.1 | 6.2 |

| | C | H | N | S | H$_2$O |
|---|---|---|---|---|---|
| Found: | 38.8 | 2.1 | 5.1 | 10.7 | 5.9 |

7-Hydroxy-1,2-naphthoquinone-2-diazide-4-sulfonic acid (K salt).1 H$_2$O (IV)

An amount of 89% 7-hydroxy-1,2-naphthoquinone-4-sulfonic acid (K salt). 1 H$_2$O (131.4 g=0.377 mol) was introduced in portions with stirring in the course of 25 minutes into a suspension of 88.2 g (0.47 mol) of p-toluenesulfonic acid hydrazide and 900 ml of methanol and stirred for a further 3 hours at 20°-28° C., during which the dark-red suspension changed to a yellow suspension. The latter was then cooled to 0 to 5° C., the crude yellow reaction product was filtered off with suction and washed on the suction filter with twice 100 ml of ethanol and the filter residue was dried for 16 hours in a circulating-air oven at 50°-55° C. The crude reaction product contained small proportions of 7-hydroxy-1,2-naphthoquinone-1-diazide-4-sulfonic acid (K salt) and 1 mol of water of crystallization. The pure 7-hydroxy-1,2-naphthoquinone-2-diazide-4-sulfonic acid (K salt) was obtained by reprecipitating the crude product from ethanol/water.

Yield: 112.5 g of crude product (95.2% quality),
107.1 g of pure product (100% quality),
i.e., 93.5% of theory.
Characteristic data
Appearance: light-yellow, crystalline powder
Melting point: ≧165° C. (decomposition)
Elemental analysis
Empirical formula: C$_{10}$H$_5$N$_2$O$_5$SK.1 H$_2$O
Molecular weight: 304

| | C | H | N | S | H$_2$O |
|---|---|---|---|---|---|
| Calculated: | 37.3 | 2.2 | 8.7 | 9.9 | 5.6 |
| Found: | 37.0 | 2.0 | 8.5 | 9.6 | 5.3 |

7-Methoxy-1,2-naphthocuinone-2-diazide-4-sulfonic acid (K salt).1 H$_2$O (V/A)

An amount of 95.2% 7-hydroxy-1,2-naphthoquinone-2-diazide-4-sulfonic acid (K salt). 1 H$_2$O (21.28 g=0.067 mol) was dissolved in 140 ml of water and 36 ml (0.072 mol) of 2 N potassium hydroxide solution. Dimethyl sulfate (13.23 g=0.105 mol) was then added at 20°-25° C. with stirring to the orange-red solution formed (pH: 12.08).

The methylation reaction, which started immediately, was indicated by a drop in the pH of the solution (pH meter). The pH of the solution was kept in a range between 11 and 12 by dropwise addition of 16.8 ml (0.034 mol) of 2 N potassium hydroxide solution by means of a graduated pipette ("pH-controlled reaction").

After about 30 minutes, light-yellow platelets having a shine like mother-of-pearl precipitated from the yellow-brown solution. The resulting suspension was first stirred for 1.5 hours at 0 to 2° C., a pH of 11.5-11.7 being established. Subsequently, the mixture was filtered with suction, and the filter residue was washed first with 20 ml of saturated potassium chloride solution and then with 15 ml of ice water and subsequently dried in a circulating-air oven at 20°-25° C. The crude reaction product still contained 1 mol of water of crystallization.

The pure 7-methoxy-1,2-naphthoquinone-2-diazide-4-sulfonic acid (K salt).1 H$_2$O can be obtained by reprecipitation of the crude product from water.

Yield: 19.95 g of crude product (91.4% quality),
18.23 g of pure product (100% quality),
i.e., 81% of theory.
Characteristic data
Appearance: yellow crystalline powder
Melting point: ≧150° C. (decomposition)
Elemental analysis
Empirical formula: C$_{11}$H$_7$N$_2$O$_5$SK.1 H$_2$O
Molecular weight: 336

| | C | H | N | S | H$_2$O |
|---|---|---|---|---|---|
| Calculated: | 39.3 | 2.7 | 8.3 | 9.5 | 5.4 |
| Found: | 38.8 | 2.5 | 8.2 | 9.5 | 5.3 |

In an analogous manner, the corresponding 1,2-naphthoquinone-2-diazide-4-sulfonic acid derivatives of the general formula A, substituted in the 7-position by ether or ester radicals, were obtained by reacting 7-hydroxy-1,2-naphthoquinone-2-diazide-4-sulfonic acid (K salt).1 H$_2$O (IV) with, respectively, various etherifying agents (B), for example diethyl sulfate, epibromohydrin or benzyl bromide, or esterifying agents (C), for example benzoyl chloride or p-toluenesulfonic acid chloride. It was possible to prepare the 7-acetyloxy derivative of the general formula A by reacting 7-hydroxy-1,2-naphthoquinone-2-diazide-4-sulfonic acid (K salt).1 H$_2$O with acetic anhydride in glacial acetic acid and anhydrous zinc chloride.

Some of the compounds according to the invention, of the general formula A, are listed in Table 1 which follows.

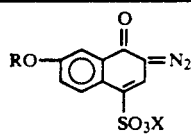

A

| R | X | Etherifying agent B Esterifying agent C | | Molar ratio IV:B | IV:C | Reaction time (hours) | Melting point (°C.) | Yield (%) | | Elemental analysis | | | | |
|---|---|---|---|---|---|---|---|---|---|---|---|---|---|---|
| | | | | | | | | | | C | H | N | S | H$_2$O |
| CH$_3$— | K | (CH$_3$O)$_2$SO$_2$ | (B) | 1:1.5 | — | 1.5 | 150 (D.) | 85 | c | 39.3 | 2.7 | 8.3 | 9.5 | 5.4 |
| | | | | | | | | | f | 38.4 | 2.2 | 8.2 | 9.5 | 5.3 |
| C$_2$H$_5$— | K | (C$_2$H$_5$O)$_2$SO$_2$ | (B) | 1:1.1 | — | 6 | 150 (D.) | 70 | c | 41.1 | 3.1 | 8.0 | 9.1 | 5.1 |
| | | | | | | | | | f | 40.6 | 2.6 | 7.7 | 9.1 | 3.2 |

-continued

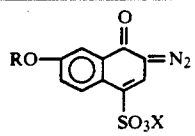

A

| R | X | Etherifying agent B Esterifying agent C | Molar ratio IV:B | Molar ratio IV:C | Reaction time (hours) | Melting point (°C.) | Yield (%) | | Elemental analysis C | H | N | S | H₂O |
|---|---|---|---|---|---|---|---|---|---|---|---|---|---|
| CH₂—CH—CH₂— \O/ | K | CH₂—CHCH₂Br \O/ | (B) 1:1.1 | — | 4.5 | 145 (D.) | 55 | c f | 43.3 42.8 | 2.5 2.5 | 7.8 7.8 | 8.9 8.7 | 4.8 4.4 |
| ⌬—CH₂— | K | ⌬—CH₂Br | (B) 1:1.1 | — | 4.5 | 120 (D.) | 62 | c f | 49.5 49.6 | 3.2 2.9 | 6.8 6.6 | 7.8 7.6 | 4.4 4.2 |
| ⌬—CO— | K | ⌬—COCl | (C) — | 1:1.15 | 2.5 | 250 (D.) | 90 | c f | 47.9 48.0 | 2.6 2.3 | 6.6 6.5 | 7.5 7.3 | 4.4 4.0 |
| CH₃⌬SO₂— | K | CH₃⌬—SO₂Cl | (C) — | 1:1.15 | 2.5 | 230 (D.) | 83 | c f | 41.3 41.3 | 3.0 2.7 | 5.7 5.5 | 13.0 12.2 | 7.9 7.4 |
| CH₃CO— | K | (CH₃CO)₂O | | | 2 | 155 (D.) | 66 | c f | 41.6 41.0 | 2.0 2.0 | 8.1 7.8 | 9.3 9.0 | — — |

D = Decomposition

7-Methoxy-1,2-naphthoquinone-2-diazide-4-sulfonic acid chloride (VI)

An amount of 91.4% 7-methoxy-1,2-naphthoquinone-2-diazide-4-sulfonic acid (K salt).1 H₂O (V) (15 g=0.0408 mol) was introduced in portions at 12°-15° C. in the course of 35 minutes into 72.5 ml (1.13 mol) of chlorosulfonic acid, and 16.35 ml (0.224 mol) of thionyl chloride were then added. The temperature of the reaction mixture rose to 18°-20°-C., with evolution of SO₂ and HCl gas. The reaction mixture was heated at 48°-50° C. for a further 15 minutes, cooled to 20° C. and then carefully added dropwise with good stirring to 680 g of ice and 230 ml of water. The mixture was filtered with suction after 3-4 hours, and the moist filter residue (about 29 g) from the suction filter was dissolved in 690 ml of acetone. The yellow-brown solution was stirred for 5 minutes at 22-24° C. with 2 g of activated carbon, the activated carbon was filtered off with suction and the clear filtrate was added dropwise in the course of 50 minutes to a mixture of 1500 ml of water and 50 ml of 36% hydrochloric acid. After 2 minutes, the product was filtered off with suction, well pressed off and dried in vacuo for 16 hours over phosphorus pentoxide.

Yield: 10.75 g of pure product, i.e. 88.3% of theory
Characteristic data
Appearance: light-yellow, finely disperse powder
Melting point: ≧165° C. (decomposition), red coloration
Elemental analysis
Empirical formula: C₁₁H₇N₂O₄SCl
Molecular weight: 298.5

| | C | H | N | S | Cl |
|---|---|---|---|---|---|
| Calculated: | 44.2 | 2.3 | 9.4 | 10.7 | 11.9 |
| Found: | 44.1 | 2.1 | 9.4 | 10.8 | 12.2 |

Condensation product of 7-methoxy-1,2-naphthoquinone-2-diazide-4-sulfonic acid chloride and 2,3,4-trihydroxy-benzophenone (VII)

7-Methoxy-1,2-naphthoquinone-2-diazide-4-sulfonic acid chloride (VI) (5.17 g=0.0173 mol) and 1.265 g (0.0055 mol) of 2,3,4-trihydroxybenzophenone were suspended in 85 ml of acetonitrile and 3.62 g (0.0358 mol) of N-methylmorpholine were added thereto with stirring in the course of 20 minutes, the starting material going into solution and the temperature rising from 22 to 28° C. Stirring was continued for a further 1.5 hours at 20°-22° C., and the dark-brown solution was then added dropwise to 500 ml of 0.1 N hydrochloric acid. The precipitated reaction product was filtered off with suction and dissolved in 200 ml of acetone. The solution was treated with activated carbon, the filtered clear yellow solution was added dropwise to 500 ml of 0.1 N hydrochloric acid, and the precipitated product was filtered off with suction and digested for 10 minutes in 200 ml of ethanol at 50-70° C. The suspension was then cooled to 20°-23° C. The reaction product purified in this way was filtered off with suction and dried at 22°-25° C. in a circulating-air oven.

Yield: 5.1 g of condensation product
Characteristic data
Appearance: light-yellow, finely pulverulent substance
Melting point: ≧150° C. (decomposition)
HPLC analysis

| Composition of the condensation product | |
|---|---|
| 4.8 g | of the triester of 2,3,4-trihydroxybenzophenone = 94% of theory |
| 0.2 g | of the diester of 2,3,4-trihydroxybenzophenone = 4% of theory |
| 0.1 g | of the monoester of 2,3,4-trihydroxybenzophenone = |

-continued

| Composition of the condensation product |
|---|
| 2% of theory. |

Elemental analysis
Empirical formula: $C_{46}H_{28}N_6O_{16}S_3$ (triester)
Molecular weight: 1016

|  | C | H | N | S |
|---|---|---|---|---|
| Calculated: | 54.3 | 2.8 | 8.3 | 9.4 |
| Found: | 53.0 | 2.6 | 7.8 | 9.7 |

What is claimed is:

1. A substituted 1,2-naphthoquinone-2-diazide-4-sulfonic acid of the formula A

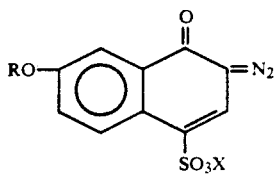

in which
R is an epoxyalkyl group having 3 to 6 carbon atoms, an alkylcarbonyl group having 2 to 6 carbon atoms or an alkylsulfonyl group having 1 to 4 carbon atoms, the carbon chains of which groups may be interrupted by at least one oxygen atom, or an aralkyl group having 7 to 10 carbon atoms, an arylcarbonyl group having 7 to 10 carbon atoms or an arylsulfonyl group having 6 to 10 carbon atoms, which groups may be substituted by alkyl, trihalogenoalkyl, alkoxy, alkylcarbonyl or alkylsulfonyl groups or halogen, and
X is one of a hydrogen, an alkali metal, an alkaline earth metal and an ammonium group.

2. A compound as claimed in claim 1, wherein X is potassium or sodium.

3. A process for preparing a substituted 1,2-naphthoquinone-2-diazide-4-sulfonic acid or a salt thereof of the formula A

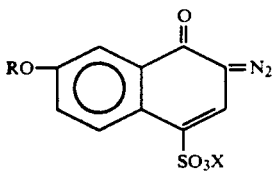

in which
R is an alkyl, epoxyalkyl, alkylcarbonyl or alkylsulfonyl group, the carbon chains of which may be interrupted by oxygen atoms, or a substituted or unsubstituted aralkyl, arylcarbonyl or arylsulfonyl group and
X is hydrogen, a metal or an ammonium group, comprising the steps of:
nitrosating 2,7-dihydroxynaphthalene;
sulfonating the resulting 2,7-dihydroxy-1-nitrosonaphthalene (I) with an alkali metal hydrogen sulfite;
reducing the bisulfite addition compound formed in acidic solution without intermediate isolation to 2,7-dihydroxy-1-aminonaphthalene-4-sulfonic acid (II);
oxidizing the 2,7-dihydroxy-1-aminonaphthalene-4-sulfonic acid to 7-hydroxy-1,2-naphthoquinone-4-sulfonic acid (III) and precipitating the acid as a salt;
converting the salt with an arylsulfonic acid hydrazide to the corresponding salt of 7-hydroxy-1,2-naphthoquinone-2-diazide-4-sulfonic acid (IV);
converting this salt in aqueous alkali at temperatures between about 20 and 30° C. and at a pH of 11-12 with an alkylating or acylating agent to the corresponding salt of the compound of formula A substituted in the 7-position;
isolating the salt.

4. The process as claimed in claim 3, wherein the nitrosation is carried out in aqueous suspension containing acetic acid with an alkali metal nitrite at temperatures between about +5 and −10° C. and the nitroso compound is isolated.

5. The process as claimed in claim 3, wherein the sulfonation is carried out with an alkali metal hydrogen sulfite or alkali metal disulfite in aqueous phase in a pH range of 5-7 and the bisulfite addition compound formed is reduced, without intermediate isolation, in an aqueous solution containing a mineral acid at temperatures between 20 and 60° C. to the corresponding aminosulfonic acid.

6. The process as claimed in claim 3, wherein the oxidation is carried out with about 15-25% by weight aqueous nitric acid at temperatures between 15 and 25° C., and the naphthoquinonesulfonic acid formed is precipitated and isolated as the ammonium salt or potassium salt.

7. The process as claimed in claim 3, the ammonium salt or potassium salt of the naphthoquinonesulfonic acid is converted with p-sulfonic acid hydrazide in aqueous or organic phase at temperatures between about 20 and 70° C. to the corresponding salt of 7-hydroxy-1,2-naphthoquinone-2-diazide-4-sulfonic acid and this salt is isolated.

8. The process as claimed in claim 3, wherein the alkylation is carried out with aliphatic or aromatic sulfonic acid esters or with alkyl, aralkyl or epoxyalkyl halides.

9. The process as claimed in claim 8, wherein a dialkyl sulfate is used as the alkylating agent.

10. The process as claimed in claim 8, wherein epoxypropyl bromide or benzyl bromide is used as the alkylating agent.

11. The process as claimed in claim 3, wherein the acylation is carried out with an aromatic carboxylic or sulfonic acid halide.

12. The process as claimed in claim 11, wherein benzoyl chloride or p-toluenesulfonic acid chloride is used as the acylating agent.

13. The process as claimed in claim 3, wherein
R is an alkyl group having 1 to 6 carbon atoms, an epoxyalkyl group having 3 to 6 carbon atoms, an alkylcarbonyl group having 2 to 6 carbon atoms or an alkylsulfonyl group having 1 to 4 carbon atoms, the carbon chains of which groups may be interrupted by at least one oxygen atom, or an aralkyl group having 7 to 10 carbon atoms, an arylcarbonyl group having 7 to 10 carbon atoms or an arylsulfonyl group having 6 to 10 carbon atoms, which groups may be substituted by alkyl, trihalogenoalkyl, alkoxy, alkylcarbonyl or alkylsulfonyl groups or halogen, and X is an alkali metal or alkaline earth metal.

14. The process as claimed in claim 13, wherein X is potassium or sodium.

15. The process as claimed in claim 4, additionally comprising the step of converting the salt formed to its corresponding acid.

* * * * *